(12) United States Patent
Nissilä et al.

(10) Patent No.: US 9,364,683 B2
(45) Date of Patent: Jun. 14, 2016

(54) PORTABLE ELECTRONIC DEVICE

(75) Inventors: Juuso Nissilä, Ii (FI); Antti Aunio, Oulu (FI)

(73) Assignee: Valkee OY (FI)

( * ) Notice: Subject to any disclaimer, the term of this patent is extended or adjusted under 35 U.S.C. 154(b) by 1309 days.

(21) Appl. No.: 12/440,141

(22) PCT Filed: Sep. 5, 2007

(86) PCT No.: PCT/FI2007/050474
§ 371 (c)(1),
(2), (4) Date: Jun. 5, 2009

(87) PCT Pub. No.: WO2008/029001
PCT Pub. Date: Mar. 13, 2008

(65) Prior Publication Data
US 2010/0042188 A1   Feb. 18, 2010

(30) Foreign Application Priority Data

Sep. 6, 2006  (FI) .................................... 20065552

(51) Int. Cl.
*A61N 5/06*   (2006.01)

(52) U.S. Cl.
CPC ............ *A61N 5/0603* (2013.01); *A61N 5/0622* (2013.01); *A61N 2005/0605* (2013.01); *A61N 2005/0628* (2013.01); *A61N 2005/0647* (2013.01)

(58) Field of Classification Search
CPC ... A61N 2005/0605; A61N 5/06; A61N 5/00; H04R 25/652; H04R 25/656; H04R 25/70; H04R 25/75
USPC ................. 607/88–93; 604/20; 381/321–331; 180/130, 135
See application file for complete search history.

(56) References Cited

U.S. PATENT DOCUMENTS

| | | | | |
|---|---|---|---|---|
| 4,865,035 A | * | 9/1989 | Mori | ................................ 607/92 |
| 5,167,228 A | | 12/1992 | Czeisler et al. | |
| 5,366,483 A | * | 11/1994 | Sadkhin | ............................ 607/3 |
| 5,712,917 A | * | 1/1998 | Offutt | ............................ 381/328 |
| 5,814,008 A | * | 9/1998 | Chen et al. | ........................ 604/21 |
| 5,893,828 A | * | 4/1999 | Uram | ............................ 600/108 |
| 6,350,275 B1 | | 2/2002 | Vreman et al. | |

(Continued)

FOREIGN PATENT DOCUMENTS

| | | |
|---|---|---|
| DE | 3823402 | 1/1990 |
| DE | 10049068 | 9/2001 |
| DE | 19947678 | 11/2001 |
| DE | 10201904 | 7/2003 |
| DE | 10307954 | 9/2004 |
| DE | 10326522 | 1/2005 |
| DE | 202006004967 | 6/2006 |
| EP | 1 074 275 | 2/2001 |
| EP | 1074275 | 7/2001 |
| GB | 2203046 | 10/1988 |
| GB | 2333962 | 11/1999 |
| JP | 10277167 | 10/1998 |
| WO | 98/51372 | 11/1998 |
| WO | 9851372 | 11/1998 |
| WO | 9956826 | 11/1999 |
| WO | 2004018040 | 3/2004 |
| WO | 2006/134339 | 12/2006 |
| WO | 2006134339 | 12/2006 |
| WO | 2007019720 | 2/2007 |
| WO | 2007/033290 | 3/2007 |
| WO | 2007050144 | 5/2007 |
| WO | 2008021692 | 2/2008 |

OTHER PUBLICATIONS

International Search Report dated Dec. 13, 2007, from corresponding PCT application.

*Primary Examiner* — Yogesh Patel
(74) *Attorney, Agent, or Firm* — Tarolli, Sundheim, Covell & Tummino LLP

(57) ABSTRACT

The portable electronic device includes radiation elements (104A, 104B) for directing optical radiation energy non-invasively at intracranial nerve tissue of a user through an external auditory canal of the user of the portable electronic device to stimulate the user's intracranial nerve tissue. Stimulation may have a metabolic and/or nervous response, which appears as a change in alertness, diurnal rhythm and in concentrations of several hormones and brain transmitters.

3 Claims, 3 Drawing Sheets

(56) References Cited

U.S. PATENT DOCUMENTS

| | | | |
|---|---|---|---|
| 6,358,272 B1 | 3/2002 | Wilden | |
| 6,795,562 B1* | 9/2004 | Gunnersen et al. | 381/325 |
| 7,950,396 B2* | 5/2011 | Rose et al. | 128/898 |
| 7,993,381 B2 | 8/2011 | Mac et al. | |
| 2002/0198577 A1 | 12/2002 | Jaillet | |
| 2003/0004499 A1 | 1/2003 | McDaniel | |
| 2003/0023284 A1 | 1/2003 | Gartstein et al. | |
| 2003/0055414 A1* | 3/2003 | Altshuler et al. | 606/9 |
| 2004/0073278 A1* | 4/2004 | Pachys | 607/88 |
| 2004/0249237 A1 | 12/2004 | Campbell et al. | |
| 2005/0107849 A1* | 5/2005 | Altshuler et al. | 607/88 |
| 2005/0137656 A1* | 6/2005 | Malak | 607/88 |
| 2005/0158687 A1* | 7/2005 | Dahm | 433/29 |
| 2005/0192478 A1 | 9/2005 | Williams et al. | |
| 2006/0167531 A1 | 7/2006 | Gertner et al. | |
| 2006/0184214 A1 | 8/2006 | McDaniel | |
| 2006/0235493 A1* | 10/2006 | Dotson | 607/89 |
| 2007/0167999 A1* | 7/2007 | Breden et al. | 607/88 |
| 2008/0319516 A1* | 12/2008 | Dougal | 607/88 |
| 2009/0319008 A1 | 12/2009 | Mayer | |
| 2010/0179469 A1 | 7/2010 | Hammond et al. | |
| 2011/0040356 A1 | 2/2011 | Schiffer | |
| 2011/0046432 A1 | 2/2011 | Simon et al. | |
| 2011/0313499 A1 | 12/2011 | Smith et al. | |

\* cited by examiner

US 9,364,683 B2

PORTABLE ELECTRONIC DEVICE

FIELD

The invention relates to a portable electronic device and a method.

BACKGROUND

Human intracranial nerve tissue includes regions that are stimulated by optical radiation directed at the regions. Stimulation may have a metabolic and/or nervous response, which appears as a change in alertness, diurnal rhythm and in concentrations of several hormones and brain transmitters. At the moment, phenomena known to be caused by changes in the amount of light include onset of copulation behaviour in wild animals and well-known seasonal affective disorder (SAD) in humans. Optical radiation may originate from nature, or optical radiation may have an artificial origin.

It is typically necessary to use artificial optical radiation when natural light is not sufficient for achieving a desired physiological effect. Artificial optical radiation may also be generated by bright light therapy devices installed in homes or workplaces, for instance.

A disadvantage of bright light therapy devices is that they are large, are restricted to a certain place, have a poor efficiency and cause disturbance to the environment. Consequently, it is useful to consider alternative techniques for achieving interaction between optical radiation and intracranial nerve tissue.

BRIEF DESCRIPTION

The object of the invention is to provide a portable electronic device and a method so as to enable easy and effective stimulation of human intracranial nerve tissues. This is achieved by a portable electronic device comprising radiation means for directing optical radiation energy non-invasively at intracranial nerve tissue of a user through an external auditory canal of the user of the portable electronic device to stimulate the user's intracranial nerve tissue.

A second aspect of the invention relates to a method of directing optical radiation energy non-invasively at intracranial nerve tissue of a user through an external auditory canal of the user of a portable electronic device to stimulate the user's intracranial nerve tissue by means of the optical radiation energy.

Preferred embodiments of the invention are described in the dependent claims.

The invention is based on using a portable electronic device in stimulating intracranial nerve tissue and directing optical radiation energy at an external auditory canal by the portable electronic device. Portability and the resulting small size enable stimulation of intracranial nerve tissue in various operating environments and conditions. Using the external auditory canal as the route for optical radiation energy enhances the access of optical radiation to the intracranial nerve tissue and no blinding radiation is directed at the user's eyes. Furthermore, use of the external auditory canal provides controlled conditions for easy adjustment of the effective power of optical radiation.

LIST OF FIGURES

The invention will now be described in greater detail in connection with preferred embodiments, with reference to the accompanying drawings, in which FIG. 1 illustrates a first example of an embodiment of a portable electronic device;

DESCRIPTION OF EMBODIMENTS

Figure 1:
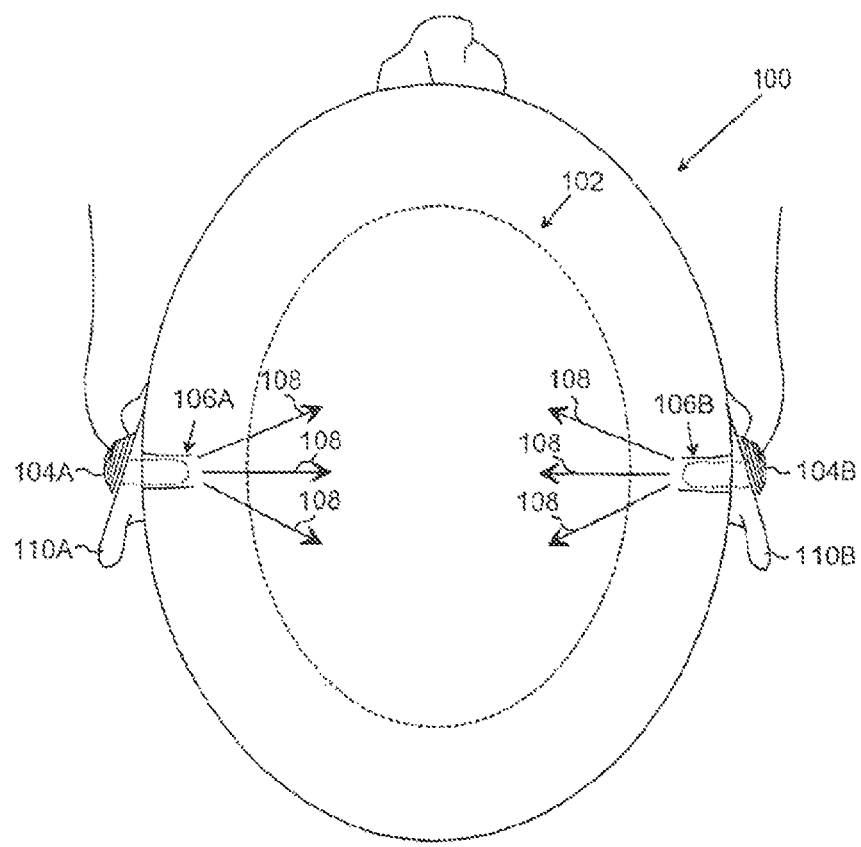

The head 100 area of a user and an example of a portable electronic device comprising radiation means 104A, 104B will be described with reference to FIG. 1.

A portable electronic device is a portable device carried by the user without an external support means. In this case external support refers, for example, to support that, resting on the ground or another fixed structure, supports the device. The user is a person capable of independently using a portable electronic device. The use comprises, for example, placing a portable electronic device on the body, switching the portable electronic device on and off and performing operating settings of the portable electronic device.

In an embodiment, the portable electronic device is user-specific, in which case the person the optical radiation is directed at controls the portable electronic device himself via a user interface, for example.

The radiation member 104A, 104B directs optical radiation 108 at the user's external auditory canal 106A, 106B, which absorbs optical radiation 108 and transmits optical radiation energy 108 to intracranial nerve tissue 102. In that case, the intracranial nerve tissue is subjected to a treatment that has a response in the intracranial nerve tissue. In this context, the terms "optical radiation" and "optical radiation energy" are equivalent concepts, and the same reference number 108 is used to denote both. Optical radiation 108 typically comprises the wavelengths of infrared radiation, visible light and ultraviolet radiation.

Propagation of optical radiation energy 108 is based on the optical propagation of radiation in tissue. When optical radiation energy 108 propagates in tissue, part of it is converted into heat. In addition, the wave-length distribution of optical radiation 108 typically changes due to absorption in tissue.

In the described solution, optical radiation energy 108 is directed at the intracranial nerve tissue 102 non-invasively. In that case, the radiation member 104A, 104B is outside the skin and does not penetrate into the user's tissue. Here also the inner surface of the external auditory canal 106A, 106B is defined as skin. Use of the external auditory canal 106A, 106B as an optical channel and use of the external auditory canal 106A, 106B walls as absorbers of optical radiation 108 enables using low optical power in illuminating the intracranial nerve tissue.

Optical radiation energy 108 is received in the radiation-sensitive intracranial nerve tissue 102, which is stimulated by the optical radiation energy 108. Stimulation typically appears as a nervous and/or hormonal response in the nerve tissue.

The intracranial nerve tissue 102 responsive to optical radiation energy 108 comprises, for example, cerebrum, cerebellum, vestibular organs, auditory organs, organs of smell, bulbus, and/or regions of autonomic regulation. The response may be based on a change in the concentration of melatonin hormone caused by the optical radiation 108, for example.

In an embodiment, the intracranial nerve tissue 102 responsive to optical radiation energy 108 comprises a pineal body, also known as a pineal gland.

In an embodiment, the intracranial nerve tissue 102 responsive to optical radiation 108 comprises a retina, whose ganglia cells may also sense light arriving from behind. Typically, the visual perception of ganglia cells is independent of seeing and not involved therein. Ganglia cells are in particular specialized for diffused light and their photosensitive pigment is melanopsin protein. When subjected to light, ganglia cells signal suprachiasmatic nucleus, which is the primary agent responsible for the diurnal rhythm.

In an embodiment, the intracranial nerve tissue 102 responsive to optical radiation energy 108 comprises a suprachiasmatic nucleus (SCN) which regulates the pineal body, which back-regulates the SCN by excreting melatonin.

It should be noted that the above-mentioned intracranial nerve tissues 102 that are responsive to optical radiation energy 108 are only examples. Some of the light also affects through other means, for example through neuroendocrinology of diurnal rhythm. Intracranial nerve tissues, also in the cranial region, have several non-specific responses to optical radiation energy 108 and the temperature increase caused by the optical radiation energy 108. Such responses include increase in the metabolism of tissues and changes in the immune response.

Figures 2, 3:
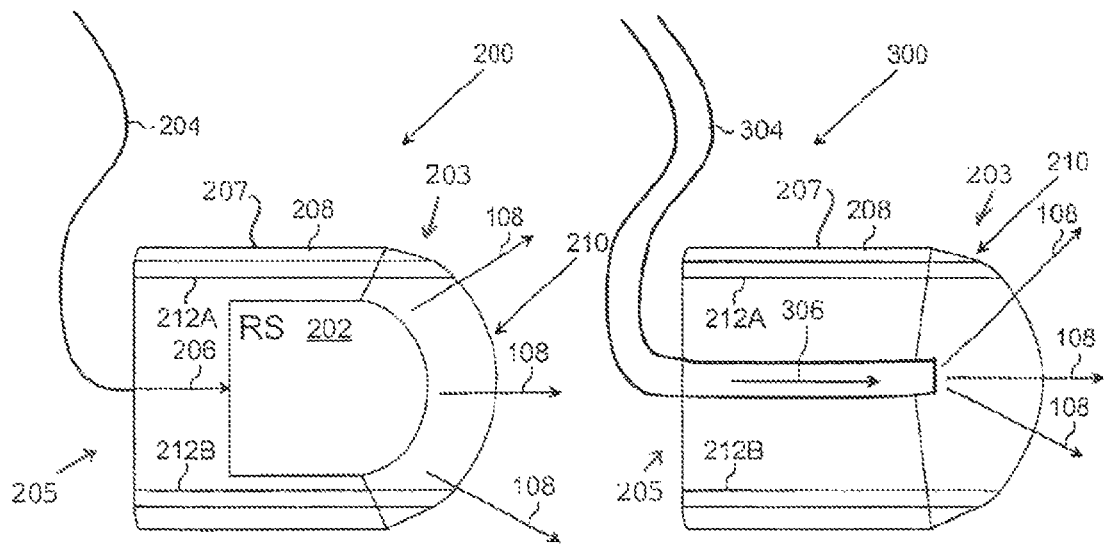
FIG. 2 illustrates a second example of an embodiment of a portable electronic device.
FIG. 3 illustrates a third example of an embodiment of a portable electronic device.

An embodiment of a radiation member 200 will be described with reference to FIG. 2, where radiation member 200 comprises a radiation source (RS) 202. FIG. 2 further illustrates an ear adapter 208 for the radiation member 200 for placing the radiation member 200 at the mouth of the external auditory canal 106A, 106B or on the earlobe 110A, 110B illustrated in FIG. 1. The ear adapter 208 is, for example, a plug-like structure which is made of plastic or rubber and which may at least partly penetrate into the user's external auditory canal 106A, 106B.

The radiation member 200 may comprise an optically permeable part 210, which allows optical radiation 108 to pass therethrough and forms a structure protecting the radiation source 202. The optically permeable part 210 may also be an opening. The ear adapter 208 has a proximal adapter end 203 including the optically permeable part 210, the ear adapter 208 having a distal adapter end 205 longitudinally separated from the proximal adapter end 203 by a longitudinally extending adapter sidewall 207, the adapter sidewall 207 having a lateral cross-sectional area which is substantially constant longitudinally between the distal adapter end 205 and the optically permeable part 210.

The radiation source 200 is an electro-optical component which converts electric power 206 into optical radiation 108. The radiation source 200 may be, for example, a bulb, light diode or diode laser. Electric power 206 may be transferred into the radiation member 202 along an electric conductor 204. The radiation member 200 may comprise one or more radiation sources 200, each of which may have a radiation source-specific spectral and/or spatial distribution of optical radiation.

In an embodiment, the spectral distribution of the radiation source 202 may be controlled. In an embodiment, the radiation source comprises RGB (red-green-blue) LEDs, which may together produce a spectrum of optical radiation at a visible wavelength. The spectral distribution of optical radiation may be weighted by controlling or driving each LED separately using a different amount of current. A corresponding LED arrangement may be implemented by infrared LEDs, for instance. The LEDs may be connected in series or in parallel. The connection in series provides the advantage that the same current passes through several LEDs, which provides savings in the total consumption of power as compared to the connection in parallel.

In an embodiment, the radiation source 202 is selected or configured so that the wavelength of the optical radiation 108 is in the area of red colour. In that case, the absorption of optical radiation 108 is slight and the amount of optical radiation directed at the intracranial nerve tissue is larger compared to a case where absorption is stronger.

In an embodiment, the radiation source 202 is selected or configured so that the wavelength of the optical radiation 108 is in the infrared area, in which case the effect of the optical radiation energy 108 is directed at target tissues sensitive to thermal radiation, such as the vestibular organ. In this case, the radiation source is an infrared diode, for instance.

In an embodiment, the radiation member 200 comprises sound channels 212A, 212B, which form an air-filled channel between the earlobe and the external auditory canal, for instance. The purpose of the sound channel 212A, 212B is to transmit air pressure differences caused by external sounds to the user's eardrum. This allows the user to hear normally as the portable electronic device according to the invention does not function as a hearing protector.

In an embodiment, the radiation member 200 is integrated into a hearing aid, in which case the radiation member 200 comprises a sound source connected to a microphone unit integrated into the radiation member 200 or separate therefrom.

In a preferred embodiment, the portable electronic device is such that at least some of the radiation members 202 or light guides 304 and at least some of the adapter means 208 form an integrated structure. In the following, three different integrated structures will be exemplified.

First, the radiation source 202 and the ear adapter 208 form an integrated structure in FIG. 2. In FIG. 2, the radiation source 202 is substantially inside the ear adapter 208.

Second, an embodiment of a radiation member 300 will be described with reference to FIG. 3 where optical radiation 306 is transmitted to the radiation member 200 along an optical light guide 304. The optical light guide 304 is, for example, an optical fibre. At an end of the optical light guide 304, there may be a lens or the end of the optical light guide 304 may be shaped so as to direct optical radiation 108 at the external auditory canal 106A, 106B in a desired manner. The portable electronic device may comprise several light guides 304, each of which may emit optical radiation 108 at a light guide-specific spectral and/or spatial distribution of the optical radiation 108. In this embodiment, the radiation member 300 may further comprise an ear adapter 208, in which case the ear adapter 208 and the end of the light guide 304 form an integrated structure.

The third way of implementing integration is the most fargoing one, i.e. the ear adapter 208 also functions as a light guide or as an end of the light guide, i.e. is capable of transmitting light into the ear. This is achieved for example by using a suitable material in the production of the ear adapter 208. In a way, this third approach is a more advanced version of the second integrated version presented above.

The three examples of integration described above could be generalized by stating that in a preferred embodiment of the portable electronic device, at least some of the radiation means 200, such as the radiation source 202 in FIG. 2, for example, or the end of the light guide 304 in connection with the radiation source, as in FIG. 3, form an integrated structure with the adapter means 208, such as an ear adapter.

An example of a control unit (CU) 400 comprising a power source (PS) 402 and a controller (CNTL) 404 will be described with reference to FIG. 4. The described embodiment of the control unit 400 may be connectable to a radiation member 200 similar to the one illustrated in FIG. 2.

The power source 402 produces electric power 206 and feeds it into the controller 404. The power source 402 is, for example, a battery, transformer or an external power source. The power source 402 may comprise a chopper for generating higher voltages from the battery voltage, for instance. The chopper enables use of low-voltage batteries and adjustment of the control voltage to be fed into a diode, for example. By adjusting the control voltage, it is possible to obtain a voltage exceeding the diode threshold voltage and a desired current to be fed into the diode.

The controller 404 receives electric energy and controls the distribution of radiation energy 108.

The controller 404 may comprise power controllers, such as transistors and/or switches for adjusting electric power 206. The controller 404 may further comprise a digital processor and memory. Encoded instructions for the digital processor for generating control commands to power controllers may be stored in the memory. The controller 404 may also comprise ASIC-circuits (Application-Specific Integrated Circuit) for generating control commands.

In an embodiment, the above-mentioned chopper is arranged in the controller 404, in which case the chopper is typically adjustable.

Chopper circuits are usually separate integrated components, which may also be partly integrated into an ASIC circuit (Application-Specific Integrated Circuit). Current mirror connection may also be used to guide a desired current accurately to different branches of a current mirror.

Furthermore, the controller 404 could include control logics for charging the battery and detect and/or monitor the battery state and provide information thereon for the user.

In an embodiment, the controller 404 controls the spatial distribution of optical radiation 108. In that case, the controller 404 may be provided with several outgoing current conductors, each of which is connected to a radiation source 202 generating a different spatial radiation distribution. By means of the spatial distribution of optical radiation 108, optical radiation 108 may be directed at a desired target tissue. The spatial distribution may be implemented by means of power controllers arranged in the controller 404, each of the power controllers being capable of independently controlling electric power 206 on the basis of commands received from the digital processor or ASIC circuits of the controller 404, for example.

In an embodiment, the controller 404 controls a temporal distribution of optical radiation 108. The temporal distribution includes short-term pulsing of electric power 206, which may be used in adjusting the short-term average power of optical radiation 108. The short term may be in the order of one second.

The temporal distribution also comprises a long-term distribution of electric power 206. The long-term distribution comprises, for example, time sequences, during which the intracranial nerve tissue 102 is treated with optical radiation energy 108. The time scale of time sequences may be minutes, hours and/or days.

The temporal distribution may be generated by modulating electric power 206 temporally. Modulation may be discrete, in which case the electric power 206 varies between on/off states. The modulation may also be continuous, in which case the electric power 206 is adjusted continuously.

The spectral distribution comprises wavelengths of optical radiation. The radiation source 200 may comprise an adjustable light element or the radiation source 200 may be provided with several light elements emitting optical radiation 108 at different frequencies. The spectral distribution may be adjusted by means of the amount of electric power 206 or by feeding electric power into a light element emitting optical radiation 108 at a desired frequency.

The controller 404 may comprise several processing programs, each of which includes instructions for different optical radiation distributions. The processing programs may be aimed at changing alertness in the following situations: changes of diurnal rhythm, treatment of jetlag, treatment of sleep irregularity caused by shift work, exceptional change of sleep rhythm, treatment of seasonal affective disorder and other affective syndromes, temporary increase of performance, waking up, alleviation of stress symptoms, nervous disorders caused by decreased light sensitivity of brain, improvement of plasticity of nerve system, treatment of sexual insufficiency.

In an embodiment, the portable electronic device further comprises a communication adapter (CA) 408 for connecting the portable electronic device to an external control device (ECD) 412. The communication adapter 408 may be arranged in the control unit 400.

The communication adapter 408 receives a command 414 from the external control device 412 and transmits the command to the controller 404. The controller 404 receives the command 404 and controls the distribution of optical radiation 108 on the basis of the command.

The communication adapter 408 may implement a wired or wireless interface. The interface may be a standardized interface, in which case the external control device 412 may be, for example, a terminal of a radio system, such as a mobile phone, PDA device (Personal Digital Assistant), desk-top computer, portable computer or music player. The wireless interface may be implemented by infrared technology, which may be based on IrDA (Infrared Data Association), or by radio technology, such as BlueTooth, ZigBee and/or BlueLite (Blue Tooth Lite).

The interface may also be based on the use of an induction loop, USB bus (Universal Serial Bus) and/or AV interface (Audio Visual).

The communication adapter 408 enables using the user interface of the external control device 412 in operating the portable electronic device. The communication adapter 408 also enables installation of control logics in the external control device 412.

In an embodiment, the portable electronic device comprises a user interface (UI) 406. The user interface 406 may be located in the control unit 400. The user interface 406 may comprise a keypad and/or display device. The user interface 406 may comprise a functionality for switching the portable electronic device on and off. Furthermore, the user interface 406 may be configured to display the state of the portable electronic device.

In an embodiment, the controller 404 comprises encoded instructions for giving instructions to the user on the intake of medicine or other chemicals. The instructions may be transmitted to the user through the user interface 406. The instructions may comprise the time for taking medicine or another chemical and/or its dose, and possibly more detailed information on the medicine or chemical. The medicine or other chemical has synergism with optical radiation 108, and thus the relative dosage of optical radiation 108 and medicine has significance for the nervous, metabolic and/or mental response.

In an embodiment, the portable electronic device comprises a charging interface for charging the battery. The charging interface may be a plug-type interface or a non-galvanic interface based on induction.

Figure 4:
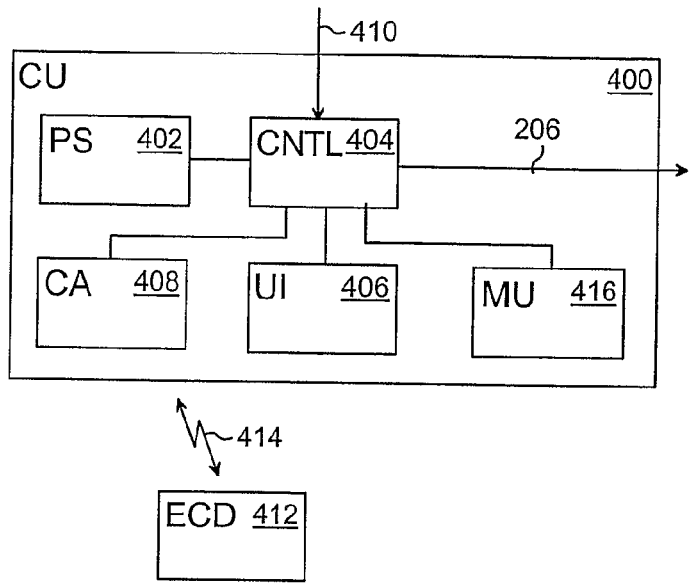
FIG. 4 illustrates a first example of an embodiment of a control unit for portable electronic device.

FIG. 4 further illustrates a measuring unit (MU) 416, which measures temperature of the external auditory canal 106A, 106B, for example. The measurement may be based on a temperature sensor, such as a semiconductor sensor or an infrared-sensitive temperature detector. The measuring unit 416 is connected to the controller 404, which monitors the temperature of the external auditory canal 106A, 106B and may adjust the power 306 of optical radiation on the basis of the temperature. This procedure allows compensating for statistical dispersion of the component properties used in the electronic device from target values, for instance. The controller 404 may optimize the power 306 of optical radiation. In an embodiment, the controller 404 prevents overheating of the external auditory canal 106A, 106B.

In an embodiment, the control device 400 is integrated into an audio player. In that case, the radiation member 200 illustrated in FIG. 2 may comprise a headset member for generating a sound signal from an electric signal. The signal processing of an audio player may be performed in the digital processor of the controller 404 by means of a computer program.

In an embodiment, the controller 404 receives measuring information 410 characterizing the user's physiological state. The controller 404 controls the distribution of optical radiation 108 on the basis of the measuring information. The measuring information 410 may be transmitted by an interface similar to a communication adapter 408.

The measuring information 410 may characterize the user's physiological state before treatment. In that case, the distribution of optical radiation 108 may be selected automatically in the controller 404 so that the treatment to be administered suits the user's current physiological state.

In an embodiment, the measuring information 410 may characterize the user's physical response to treatment. In that case, the controller 404 may select the distribution of optical radiation 108 so that the distribution suits the user's current physiological state. This embodiment refers to physiological feedback.

The measuring information typically characterizes the user's alertness. If alertness indicates a decrease in alertness in a situation where an increased or normal alertness is desirable, the dose of optical radiation 108 may be increased. If alertness indicates a decrease in alertness in a situation where a low alertness is desirable, the dose of optical radiation 108 may be reduced.

The controller 404 may comprise encoded instruction for analysing the measuring information 410 and for selecting the distribution of optical radiation 108 on the basis of the analysis.

In an embodiment, the physiological measuring information 410 comprises snoring information on the user's snoring. The snoring information includes snoring strength and temporal variation in snoring.

In an embodiment, the measuring information 410 comprises information on the user's heart rate, such as the heart rate frequency and/or variation in the heart rate. The heart rate information may be generated by a portable heart rate meter, for example.

In an embodiment, the measuring information 410 comprises the user's blood pressure.

In an embodiment, the measuring information 410 comprises the user's blood oxygen saturation.

In an embodiment, the measuring information 410 comprises the user's blood sugar level.

In an embodiment, the measuring information 410 comprises the user's encephalogram.

In an embodiment, the measuring information 410 comprises the user's skin electro conductivity.

In an embodiment, the measuring information 410 comprises the user's breathing frequency.

In an embodiment, the measuring information 410 comprises the user's eye movements.

In an embodiment, the measuring information 410 comprises the user's limb movements.

In an embodiment, the measuring information comprises the user's temperature parameter characterizing the user's body temperature, such as the inner temperature. The temperature may characterize, for example, the user's rectal temperature, eardrum temperatures and/or oesophagus temperature.

Figure 5:
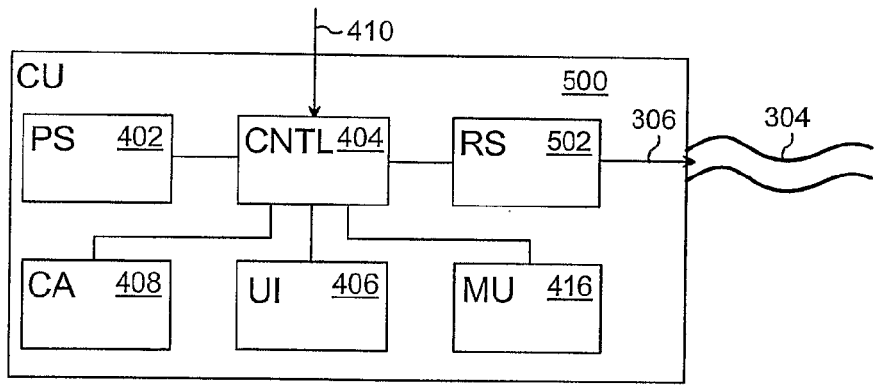
FIG. 5 illustrates a second example of an embodiment of a control unit for portable electronic device.

An embodiment of the control unit 500 comprising a radiation source 502 connected to the controller 404 will be described with reference to FIG. 5. The radiation source 502 is connected to a light guide 304, which guides the optical radiation 306 to the radiation member 300 of FIG. 3. The control unit 500 may comprise several radiation sources 502, each of which may have a characteristic spectral distribution of optical radiation 306. In this case, the spatial distribution is achieved by configuring the end of the light conductor 306 or by means of lenses in the radiation element 300. The radiation source 502 may have spectral properties similar to those of the radiation source 202 of FIG. 2.

Figure 6:
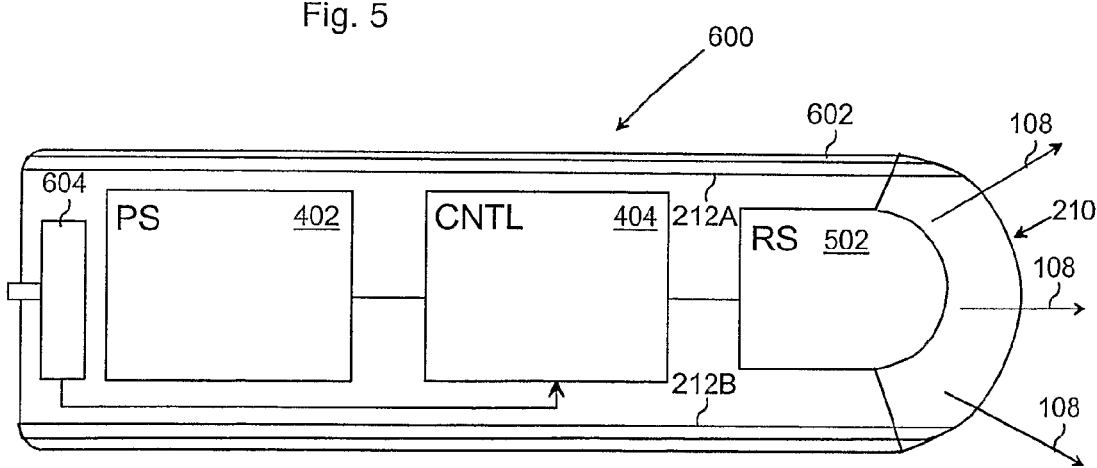
FIG. 6 illustrates a fourth example of an embodiment of a portable electronic device.

Referring to the example of FIG. 6, in an embodiment the portable electronic device 600 is an independent functional unit to be placed in the user's external ear. The independent functional unit is capable of functioning independently without an external control device and comprises a power source 402, controller 404 and radiation source 502. The portable electronic device 600 may further comprise a switch 604 for giving commands to the controller 404 to start, end or activate treatment, for instance. In this case, the portable electronic device 600 may be implemented as a plug-like structure where the ear adapter 602 at least partly penetrates into the user's external auditory canal 106A, 106B or into the mouth of the external auditory canal 106A, 106B and holds the portable electronic device 600 in place without external support. The ear adapter 602 may be made of plastic or rubber, for instance. The independent functional unit enables a simple structure of the portable electronic device 600 and consequently low production costs. In that case, the portable electronic device 600 may be intended to be a disposable device distributed or sold at airports, for example, for alleviation of the symptoms of jetlag.

Figure 7:
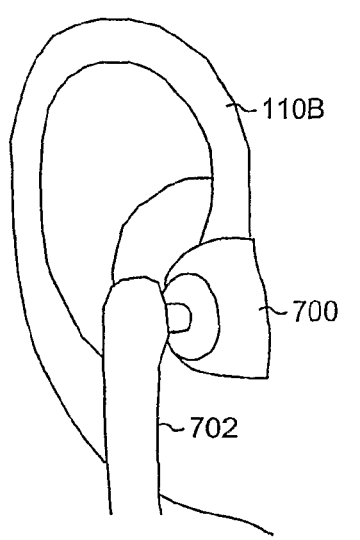
FIG. 7 illustrates a fifth embodiment of an embodiment of a portable electronic device.
Figure 8:
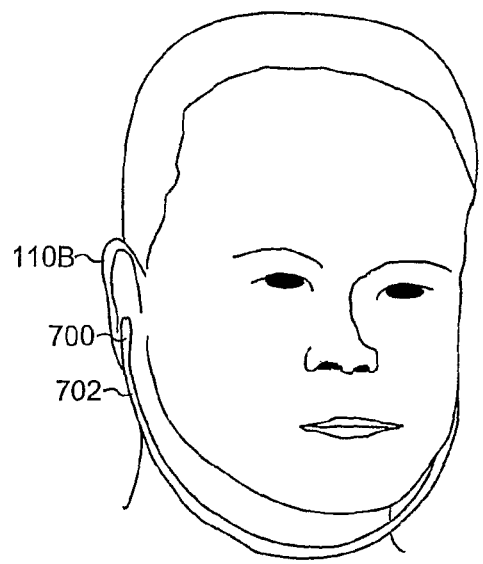
FIG. 8 illustrates a sixth example of an embodiment of a portable electronic device.

An embodiment of the described solution will be described with reference to FIGS. 7 and 8 where the portable electronic device comprises an earpiece 700 to be placed in the user's external ear 110B. The earpiece is typically a device placed at the point where the earlobe 110B meets the external auditory canal 106B and having a circular shaped or a shape corresponding to that of the earlobe. The earpiece may be supported by a headband structure 702, which may be connected to the earpiece intended for the other ear. Inside the headband structure 702, there may be electric or optical conductors. The headband structure 702 may be made of plastic or metal.

In all the above-mentioned embodiments, the electronic device may comprise radiation members for one or more ears.

In an embodiment, the ear adapter of the electronic device comprises a dome-shaped structure which encloses the earlobe 110A, 110B. The dome-like ear adapter enables accurate positioning of the radiation source, and the radiation source may be outside the ear but directed so that the optical radiation focuses on the external auditory canal 106A, 106B.

Figure 9:
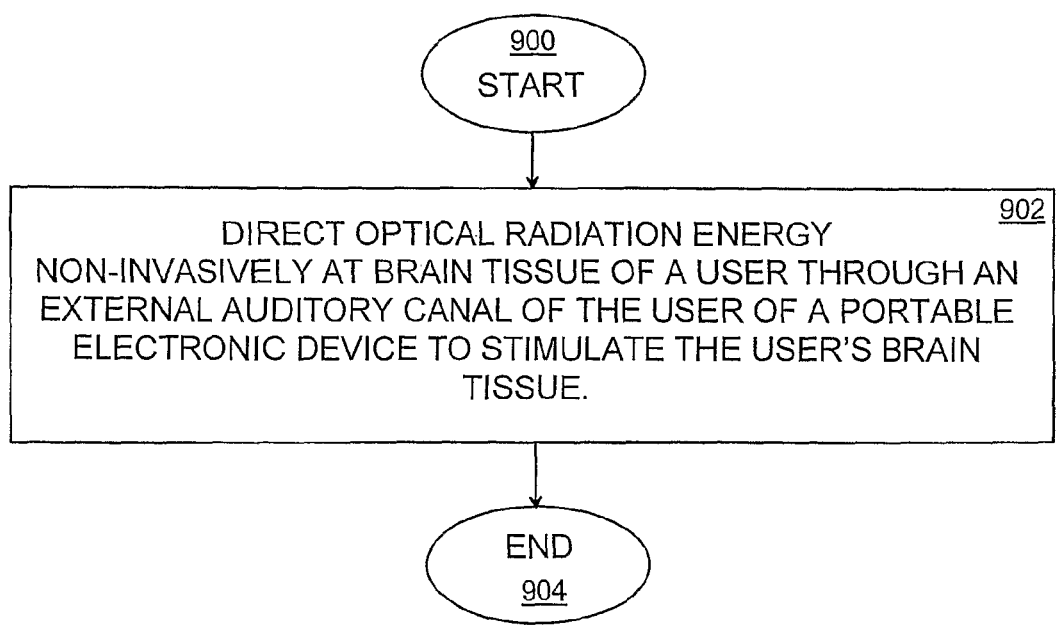
FIG. 9 illustrates an example of an embodiment of a method.

An embodiment of the method according to the presented solution will be described with reference to FIG. 9.

The method starts in 900.

In 902, a portable electronic device directs optical radiation energy 108 non-invasively at intracranial nerve tissue 102 of a user through an external auditory canal 106A, 106B of the user of the portable electronic device to stimulate the user's intracranial nerve tissue 102.

The method ends in 904.

Even though the invention was described above with reference to an example according to the enclosed drawings, it is clear that the invention is not restricted thereto but may be modified in various ways within the scope of the appended claims.

The invention claimed is:

1. A portable electronic device configured to penetrate into a user's external auditory canal comprising:
   an optical radiation source comprising a plurality of LEDs;
   radiation means for directing optical radiation energy from the optical radiation source non-invasively at intracranial nerve tissue of a user through an external auditory canal of the user of the portable electronic device to stimulate the user's intracranial nerve tissue, the radiation means comprising a light guide connected to the optical radiation source for guiding optical radiation from the optical radiation source into the external auditory canal, the radiation means also comprising an ear adapter having a proximal adapter end including an optically permeable part, the ear adapter having a distal adapter end longitudinally separated from the proximal adapter end by a longitudinally extending adapter sidewall, the adapter sidewall having a lateral cross-sectional area which is substantially constant longitudinally between the distal adapter end and the optically permeable part; and
   a controller which is connected to the radiation means and to the optical radiation source and includes processing programs configured for controlling spectral distribution via individually controlling current to at least two of the plurality of LEDs.

2. The portable electronic device of claim 1, comprising a control unit comprising the optical radiation source connected to the controller, the control unit connected to a light guide which guides the optical radiation from the optical radiation source to the radiation means.

3. The portable electronic device of claim 2, wherein the control unit is spaced apart from the ear adapter, and the control unit and ear adapter are connected together by at least one light guide.

* * * * *